(12) United States Patent
Watanabe et al.

(10) Patent No.: US 12,670,803 B2
(45) Date of Patent: Jun. 30, 2026

(54) LEARNING SYSTEM, LEARNING METHOD, AND LEARNING PROGRAM

(71) Applicant: NATIONAL INSTITUTE OF INFORMATION AND COMMUNICATIONS TECHNOLOGY, Tokyo (JP)

(72) Inventors: Hiroki Watanabe, Tokyo (JP); Yasushi Naruse, Tokyo (JP)

(73) Assignee: NATIONAL INSTITUTE OF INFORMATION AND COMMUNICATIONS TECHNOLOGY, Tokyo (JP)

( * ) Notice: Subject to any disclaimer, the term of this patent is extended or adjusted under 35 U.S.C. 154(b) by 800 days.

(21) Appl. No.: 17/927,687

(22) PCT Filed: Jun. 15, 2021

(86) PCT No.: PCT/JP2021/022762
§ 371 (c)(1),
(2) Date: Nov. 23, 2022

(87) PCT Pub. No.: WO2021/261342
PCT Pub. Date: Dec. 30, 2021

(65) Prior Publication Data
US 2023/0177973 A1     Jun. 8, 2023

(30) Foreign Application Priority Data

Jun. 26, 2020     (JP) ................................. 2020-110897

(51) Int. Cl.
*G09B 7/04*          (2006.01)
*A61B 5/16*          (2006.01)
(Continued)

(52) U.S. Cl.
CPC .................. *G09B 7/04* (2013.01); *A61B 5/16* (2013.01); *A61B 5/165* (2013.01); *A61B 5/369* (2021.01);
(Continued)

(58) Field of Classification Search
CPC ... G09B 7/02; G09B 7/00; G09B 7/04; G09B 7/08; A61B 5/165; A61B 5/375; A61B 5/16; A61B 5/369; G06Q 50/20
See application file for complete search history.

(56) References Cited

U.S. PATENT DOCUMENTS 6,147,648 A     11/2000  Granholm et al.
9,953,650 B1 *   4/2018  Falevsky ................. G10L 15/22
(Continued)

FOREIGN PATENT DOCUMENTS

CN          108666743          10/2018
JP          2006-23566          1/2006
(Continued)

OTHER PUBLICATIONS

International Search Report dated Aug. 24, 2021, for PCT/JP2021/022762, 4 pages.
(Continued)

*Primary Examiner* — Jack Yip
(74) *Attorney, Agent, or Firm* — Nixon & Vanderhye PC

(57) ABSTRACT

A learning system according to one aspect of the present invention presents a question to a learner, receives an answer to the question from the learner, and after answering is complete, presents the correct answer of the question to the learner. In a case where the learner's answer to the presented question is incorrect, the learning system acquires measurement data of brain waves from when the correct answer to the incorrectly answered question was presented to the learner, and calculates the intensity of feedback-related
(Continued)

negativity from the acquired measurement data. In accordance with the calculated intensity of the feedback-related negativity and the incorrectly answered question, the learning system acquires the next question to be presented.

12 Claims, 6 Drawing Sheets

(51) Int. Cl.

| | |
|---|---|
| A61B 5/369 | (2021.01) |
| A61B 5/375 | (2021.01) |
| G06Q 50/20 | (2012.01) |
| G09B 7/00 | (2006.01) |
| G09B 7/02 | (2006.01) |
| G09B 7/08 | (2006.01) |

(52) U.S. Cl.
CPC .............. *A61B 5/375* (2021.01); *G06Q 50/20* (2013.01); *G09B 7/00* (2013.01); *G09B 7/02* (2013.01); *G09B 7/08* (2013.01)

(56) References Cited

U.S. PATENT DOCUMENTS

| | | | | |
|---|---|---|---|---|
| 2005/0191605 | A1* | 9/2005 | Nguyen ................... | G09B 7/02 434/188 |
| 2009/0049089 | A1 | 2/2009 | Adachi et al. | |
| 2012/0052476 | A1* | 3/2012 | Graesser .................. | G09B 7/04 434/362 |
| 2014/0227675 | A1* | 8/2014 | Budhu ..................... | G09B 7/02 434/362 |
| 2015/0325133 | A1* | 11/2015 | Gaglani ................... | G09B 7/00 434/322 |
| 2016/0225274 | A1* | 8/2016 | Vahid ....................... | G09B 7/02 |
| 2017/0330475 | A1 | 11/2017 | Minoda et al. | |
| 2019/0051201 | A1* | 2/2019 | Jo ............................ | G09B 5/06 |
| 2020/0367798 | A1* | 11/2020 | Frolov ................... | A61B 5/165 |
| 2022/0223062 | A1* | 7/2022 | Kodama ................. | G09B 7/02 |

FOREIGN PATENT DOCUMENTS

| | | |
|---|---|---|
| JP | 2017-207733 | 11/2017 |
| JP | 2018-124483 | 8/2018 |
| WO | 2007/066451 | 6/2007 |
| WO | 2020/105413 | 5/2020 |

OTHER PUBLICATIONS

Written Opinion of the ISA dated Aug. 24, 2021, for PCT/JP2021/022762, 3 pages.
Jun. 21, 2024 Search Report issued in European Patent Application No. 21829416.3, pp. 1-9.

* cited by examiner

Present questions

Receive answers

Present correct answers

Measure intensity of FRN when correct
answer is presented for incorrectly
answered question

S

L

Learning system    ~1

| Identifier | Difficulty level | Question | Correct Answer |
|------------|------------------|----------|----------------|
| a001 | 1 | **** | **** |
| a002 | 2 | **** | **** |
| ⋮ | ⋮ | ⋮ | ⋮ |

LEARNING SYSTEM, LEARNING METHOD, AND LEARNING PROGRAM

CROSS-REFERENCE TO RELATED APPLICATIONS

This application is the U.S. national phase of International Application No. PCT/JP2021/022762 filed Jun. 15, 2021 which designated the U.S. and claims priority to JP 2020-110897 filed Jun. 26, 2020, the entire contents of each of which are hereby incorporated by reference.

TECHNICAL FIELD

The present invention relates to a learning system, a learning method, and a learning program.

BACKGROUND AND SUMMARY

Conventional learning systems use a method where the difficulty level of questions is selected by learners themselves or is selected based on a behavioral index, such as the percentage of correct answers, to adaptively determine which questions are to be presented to learners. However, with this method, it is difficult to objectively evaluate psychological aspects of learners, such as their learning motivation. As one example, for a question being answered, it is difficult to objectively evaluate whether a learner is bored and unmotivated or conversely has high learning motivation. This means that with conventional learning systems, it has been difficult to adopt a question setting strategy that increases the learning motivation of the learner based on an objective index.

On the other hand, in recent years, development has progressed into a method that observes the state of a learner based on an objective index, such as brain waves, and selects suitable questions for the learner's state according to the obtained observation results. As one example, Patent Literature 1 (JP 2018-124483A) proposes a method of measuring the brain waves of a learner and estimating the degree of concentration and degree of deliberation from brain wave patterns. According to this method, it is possible to use brain waves as an objective index and adopt a question setting strategy that increases the learning motivation of the learner.

The inventors of the present invention found that the learning system using brain waves proposed in Patent Literature 1 and the like has the following problems. That is, correspondence between the learner's state and brain wave patterns is not exhibited, and it is unclear whether it is possible to appropriately evaluate the learner's degree of concentration and degree of deliberation based on brain wave patterns. There is also the possibility of accurate analysis of brain wave patterns making a learning system complicated (as one example, the arithmetic processing will become sophisticated require a high-powered and computational unit).

According to one aspect, the present invention was conceived in view of the situation described above, and has an object of providing a technology that uses brainwaves to select a problem-setting strategy capable of easily and appropriately increasing the learning motivation of a learner.

To solve the problem indicated above, the present invention uses the following configurations.

A learning system according to one aspect of the present invention includes: a question acquisition unit configured to acquire one or more first questions; a question presentation unit configured to present the acquired one or more first questions to a learner; an answer reception unit configured to receive answers to the presented first questions from the learner; a correct answer presentation unit configured to present correct answers for the first questions to the learner after the answers to the first questions have been received; and an intensity calculation unit configured to acquire, in a case where an answer by the learner to a first question is incorrect, measurement data generated by measuring brain activity of the learner in a case where the correct answer was presented, and calculate an intensity of feedback-related negativity from the acquired measurement data. The question acquisition unit acquires one or more second questions in accordance with the calculated intensity of feedback-related negativity and the first question that was incorrectly answered, the question presentation unit presents the acquired one or more second questions to the learner, and the answer reception unit receives an answer to each presented second question from the learner.

From the experimental example described later, the present inventors discovered that the intensity of feedback-related negativity (hereinafter also indicated as "FRN") induced when the correct answer to an incorrectly answered question was presented to a learner is useful as an objective index for evaluating the learning motivation of the learner. The intensity of FRN can be measured and calculated comparatively easily. This means that according to the learning system of the configuration described above, based on the above finding, it is possible to adopt a question setting strategy that increases the learning motivation of a learner easily and appropriately using brain waves.

In the learning system according to the above aspect, in a case where the calculated intensity of the feedback-related negativity exceeds a first threshold, the question acquisition unit may acquire, as the second questions, other questions of the same level as the first question that was incorrectly answered. According to this configuration, it is possible to continuously set questions of a level evaluated as providing high learning motivation to the learner based on the intensity of FRN.

In the learning system according to the above aspect, in a case where the calculated intensity of the feedback-related negativity is below a second threshold, the question acquisition unit may acquire, as the second questions, other questions of a different level to the first question that was incorrectly answered. According to this configuration, by setting questions of a different level to questions evaluated as providing low learning motivation to the learner based on the intensity of FRN as the next questions, it is possible to find questions of a level that provides high learning motivation.

In the learning system according to the above aspect, the learning system may further include a stopping unit configured, in a case where presentation of questions to the learner by the question presentation unit is repeated and the calculated intensity of the feedback-related negativity is continuously lower than a third threshold, to stop the repeated presentation of the questions. According to this configuration, it is possible to stop the presentation of questions and encourage the learner to take a break when the learning motivation of the learner has been continuously evaluated as being low based on the intensity of FRN.

The learning systems according to the configurations described above may be constructed of one or a plurality of computers. Also, aside from the learning systems of the configurations described above, other aspects of the present invention may include an information processing method that realizes all or part of the configurations described above, a program, and a storage medium on which such a program is stored and which is readable by a computer or other device, machine, or the like. Here, the storage medium that is readable by a computer or the like is a medium in which information such as a program is stored by an electrical, magnetic, optical, mechanical, or chemical action.

As one example, a learning method according to one aspect of the present invention is an information processing method in which a computer executes: a step of acquiring one or more first questions; a step of presenting the acquired one or more first questions to a learner; a step of receiving answers to the presented first questions from the learner; a step of presenting correct answers for the first questions to the learner after the answers to the first questions have been received; a step of acquiring, in a case where an answer by the learner to a first question is incorrect, measurement data generated by measuring brain activity of the learner in a case where the correct answer was presented; a step of calculating an intensity of feedback-related negativity from the acquired measurement data; a step of acquiring one or more second questions in accordance with the calculated intensity of feedback-related negativity and the first question that was incorrectly answered; a step of presenting the acquired one or more second questions to the learner; and a step of receiving an answer to each presented second question from the learner.

Also, as one example, a learning program according to one aspect of the present invention is a program that causes a computer to execute: a step of acquiring one or more first questions; a step of presenting the acquired one or more first questions to a learner; a step of receiving answers to the presented first questions from the learner; a step of presenting correct answers for the first questions to the learner after the answers to the first questions have been received; a step of acquiring, in a case where an answer by the learner to a first question is incorrect, measurement data generated by measuring brain activity of the learner in a case where the correct answer was presented; a step of calculating an intensity of feedback-related negativity from the acquired measurement data; a step of acquiring one or more second questions in accordance with the calculated intensity of feedback-related negativity and the first question that was incorrectly answered; a step of presenting the acquired one or more second questions to the learner; and a step of receiving an answer to each presented second question from the learner.

According to the present invention, it is possible to provide a technology that makes it possible to adopt a question setting strategy that increases the learning motivation of a learner easily and appropriately using brain waves. This is an advantageous effect.

BRIEF DESCRIPTION OF THE DRAWINGS

FIG. 4 schematically depicts an example configuration of a question database according to the present embodiment;

DETAILED DESCRIPTION

An embodiment according to one aspect of the present invention (hereinafter, referred to as "the present embodiment") is described below with reference to the drawings. However, the embodiment described below represents in every way a mere example of the present invention. It should be obvious that various improvements and modifications can be made without departing from the scope of the present invention. That is, when implementing the present invention, a specific configuration suited to that particular implementation may be adopted as appropriate. Note that although data that appears in the present embodiment is indicated using natural language, in more specific terms, data is specified in a pseudo language, commands, parameters, machine language, and the like that can be recognized by a computer.

1. Example Application

Figure 1:
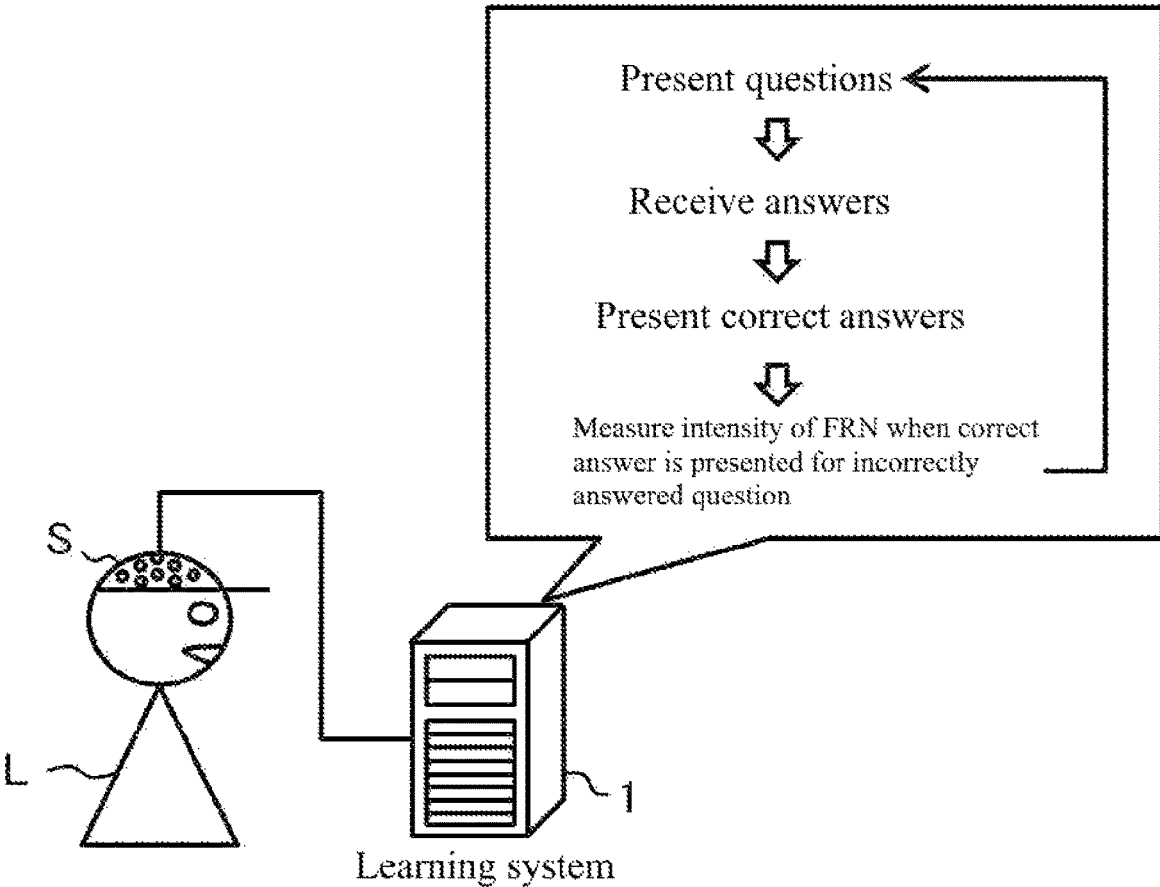
FIG. 1 schematically depicts an example situation where the present invention is applied.

FIG. 1 schematically depicts an example situation where the present invention is applied. A learning system 1 is a computer configured to provide a series of learning processes in which questions are presented to a learner L, answers are received, and feedback on whether the answers are correct or incorrect is provided.

In more detail, the learning system 1 according to the present embodiment acquires one or more questions and presents the acquired one or more questions to the learner L. The learning system 1 according to the present embodiment receives answer(s) to the presented question(s) from the learner L. After receiving the answer(s) to the question(s), the learning system 1 presents the learner L with the correct answer to each question.

If the learner L's answer to a question was incorrect, the learning system 1 acquires measurement data generated by measuring brain activity of the learner L when a correct answer was presented. In the present embodiment, the learner L wears a measurement sensor S configured to measure brain waves, and the measurement sensor S is connected to the learning system 1. The learning system 1 is capable of acquiring the measurement data from this measurement sensor S.

The learning system 1 calculates the intensity of feedback-related negativity from the acquired measurement data. The learning system 1 obtains one or more following questions in accordance with the calculated intensity of the feedback-related negativity and the question that was answered incorrectly. After this, the learning system 1 presents the obtained one or more following questions to the learner L and receives answer(s) to the presented question(s) from the learner L.

Note that a first question provided for FRN measurement is one example of a "first question" for the present invention and a subsequent question provided based on FRN intensity is one example of a "second question" for the present invention. After being presented to the learner L, a second question may be treated as a first question. That is, when the series of learning processes mentioned above is repeated, the FRN intensity is also calculated for a second question that has been provided, and further questions may be obtained in keeping with the calculated FRN intensity and the second question.

As described above, in the present embodiment, the following question to be provided is determined based on the feedback-related negativity induced when the learner L was presented with the correct answer to a question that was incorrectly answered. According to the intensity of the feedback-related negativity, it is possible to objectively evaluate the learning motivation of the learner L. The intensity of the feedback-related negativity can be measured and calculated comparatively easily. This means that according to the present embodiment, it is possible to adopt a question setting strategy that increases the learning motivation of the learner L easily and appropriately using brain waves.

2. Example Configuration

Hardware Configuration

Figure 2:
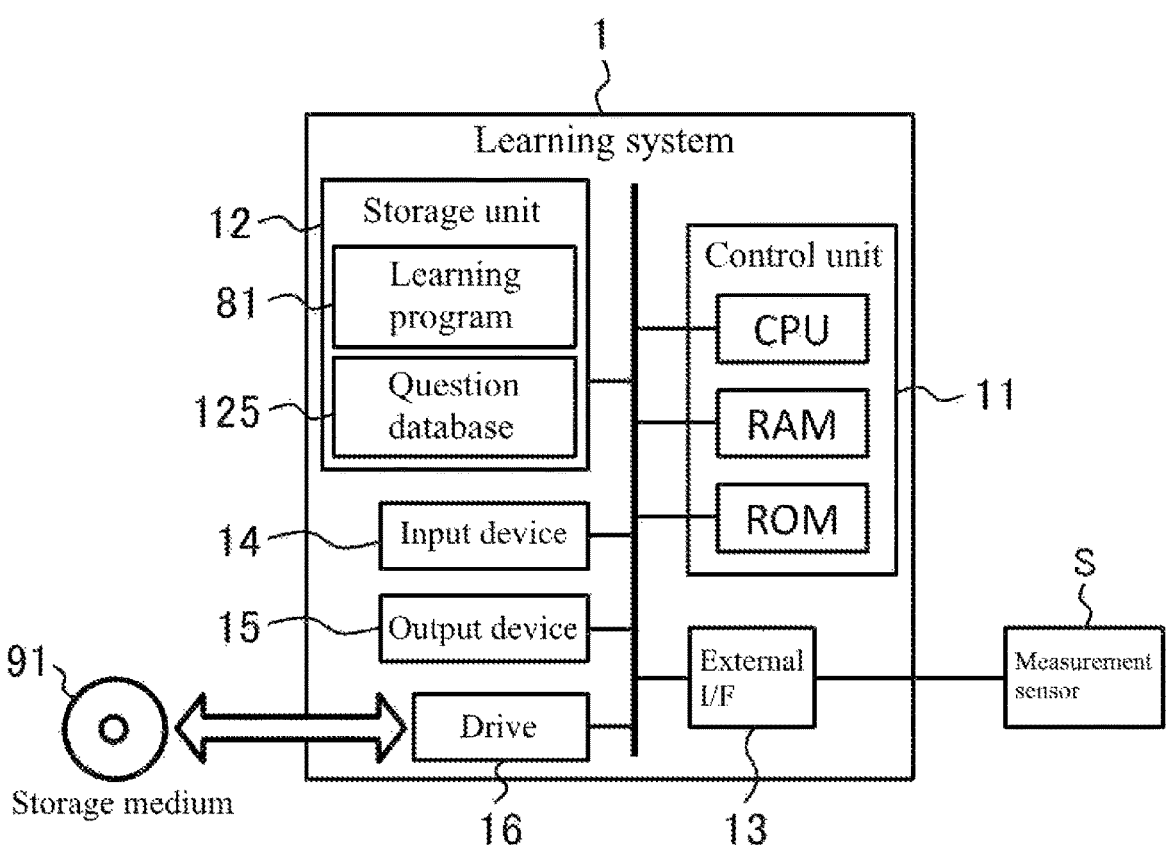
FIG. 2 schematically depicts one example hardware configuration of a learning system according to an embodiment.

FIG. 2 schematically depicts one example hardware configuration of the learning system 1 according to the present embodiment. The learning system 1 according to the present embodiment is a computer in which a control unit 11, a storage unit 12, an external interface 13, an input device 14, an output device 15, and a drive 16 are electrically connected. Note that in FIG. 2, the external interface is indicated as "external I/F".

The control unit 11 includes a CPU (Central Processing Unit) that is a hardware processor, RAM (Random Access Memory), ROM (Read Only Memory), and the like, and is configured to execute information processing based on a program and various data. The storage unit 12 is one example of a memory, and as examples is composed of a hard disk drive or a solid state drive. In the present embodiment, the storage unit 12 stores various information such as a learning program 81 and a question database 125.

The learning program 81 is a program for causing the learning system 1 to execute information processing (see FIG. 5), described later, which provides the learner L with a series of learning processes. The learning program 81 includes a series of instructions for this information processing. In the question database 125, questions and correct answers to be provided to the learner L are stored separately according to difficulty level. Difficulty level is one example of a "level" for the present invention and will be described in detail later.

The external interface 13 is an interface for connecting to an external device and as examples, is a USB (Universal Serial Bus) port or a dedicated port. The types and number of external interfaces 13 may be freely selected. In the present embodiment, the learning system 1 is connected via the external interface 13 to the measurement sensor S.

So long as it is possible to acquire measurement data for brain waves from which the intensity of the feedback-related negativity can be derived, there are no particular limitations on the type of the measurement sensor S and the measurement sensor S may be appropriately selected according to the specific implementation. As examples, the measurement sensor S may be a plate electrode coated with conductive gel or a dry electrode.

Note that the method of connecting the learning system 1 and the measurement sensor S is not necessarily limited to the example given here. As another example, when the learning system 1 and the measurement sensor S (or another computer to which the measurement sensor S is connected) are each equipped with a communication interface, the learning system 1 and the measurement sensor S may be connected via their communication interfaces.

The input device 14 is a device for inputting, for example, a mouse, keyboard, touch panel display, or microphone. The output device 15 is a device for outputting, for example, a display (a regular display or touch panel display) or a speaker. The input device 14 and the output device 15 may be integrally constructed of a touch panel display. The learning system 1 may include a plurality of input devices 14 and output devices 15. The input device 14 is used to receive answers. The output device 15 is used to present questions and correct answers.

The drive 16 is a CD drive or a DVD drive, for example, and is a drive device for reading various information, such as programs, stored on a storage medium 91. The storage medium 91 is a medium that stores various information, such as programs, by an electrical, magnetic, optical, mechanical, or chemical action so that a computer or other device, machine, or the like can read the stored various information, such as programs. At least one of the learning program 81 and the question database 125 described above may be stored on the storage medium 91. The learning system 1 may acquire at least one of the learning program 81 and the question database 125 described above from the storage medium 91. Note that in FIG. 2, a disk-type storage medium such as a CD or DVD is illustrated as one example of the storage medium 91. However, the storage medium 91 is not limited to a disk-type medium, and may be a non-disk medium. Semiconductor memory, such as flash memory, can be given as one example of a storage medium that is a non-disk medium. The type of drive 16 may be freely selected according to the type of storage medium 91.

Note that regarding the specific hardware configuration of the learning system 1, it is possible to omit, replace, and add components as appropriate according to the actual implementation. As one example, the control unit 11 may include a plurality of hardware processors. The hardware processors may be composed of microprocessors, field-programmable gate arrays (FPGA), or the like. The storage unit 12 may be composed of RAM and ROM included in the control unit 11. At least one of the external interface 13, the input device 14, the output device 15, and the drive 16 may be omitted. The learning system 1 may be composed of a plurality of computers. In this case, the hardware configuration of each computer may be the same or may differ. In place of an information processing device that has been designed specifically for the service to be provided, the learning system 1 may be a general-purpose server device, a desktop PC (Personal Computer), a mobile terminal (as examples, a mobile phone, such as a smartphone, or a tablet PC), or the like. When the learning system 1 is a server device, the learning system 1 may be configured to provide the learner L with a series of learning processes via a client device (or "user terminal").

Software Configuration

Figure 3:
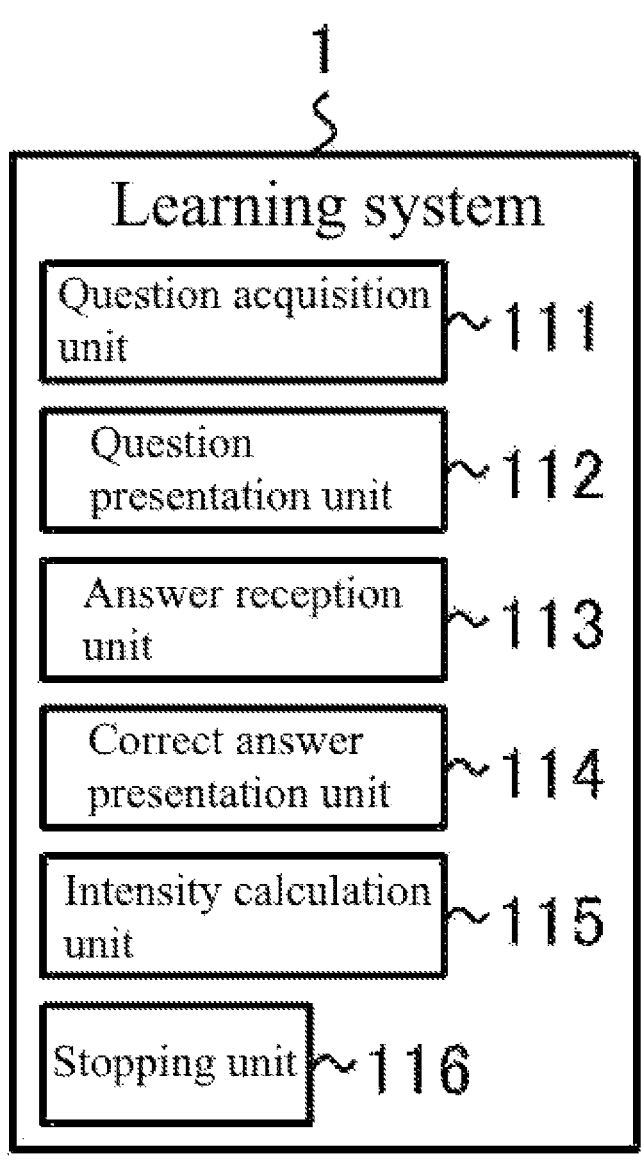
FIG. 3 schematically depicts an example software configuration of the learning system according to the present embodiment.

FIG. 3 schematically depicts an example software configuration of the learning system 1 according to the present embodiment. The control unit 11 of the learning system 1 loads the learning program 81 stored in the storage unit 12 into the RAM. The control unit 11 then causes the CPU to interpret and execute instructions included in the learning program 81 loaded into the RAM, and controls the respective components. By doing so, the learning system 1 according to the present embodiment operates as a computer equipped with a question acquisition unit 111, a question presentation unit 112, an answer reception unit 113, a correct answer presentation unit 114, an intensity calculation unit 115, and a stopping unit 116 serving as software modules.

The question acquisition unit 111 acquires one or more first questions. The question presentation unit 112 presents the acquired one or more first questions to the learner L. The answer reception unit 113 accepts answers to the presented first questions from the learner L. The correct answer presentation unit 114 presents the correct answer of a first question to the learner L after the answer to the first question has been received. When the learner L's answer to the first question is incorrect, the intensity calculation unit 115 acquires measurement data generated by measuring the brain activity of the learner L when the correct answer was presented, and calculates the intensity of the feedback-related negativity from the acquired measurement data.

The question acquisition unit 111 acquires one or more second questions according to the calculated intensity of the feedback-related negativity and the first question that was incorrectly answered. In the present embodiment, the question acquisition unit 111 can acquire the first questions and the second questions from the question database 125. The question presentation unit 112 presents the acquired one or more second questions to the learner L. The answer reception unit 113 receives answer(s) to the presented second question(s) from the learner L. The presentation of questions to the learner L (that is, the series of learning processes) is repeated by the question presentation unit 112, and when the calculated intensity of the feedback-related negativity is continuously lower than a threshold, the stopping unit 116 stops the repeated presentation of questions.

FIG. 4 schematically depicts an example configuration of the question database 125 according to the present embodiment. In the example in FIG. 4, the question database 125 is structured in a table format in which each record has fields for storing various types of information, such as an identifier, a difficulty level, a question, and a correct answer. The identifier is used to identify the data in each record. The scale of the difficulty level may be set freely. The format of questions may be determined as appropriate according to the implementation. As examples, the question types may include calculation questions, multiple choice questions, and written questions. The learner L to whom the questions are to be provided may be appropriately selected according to the implementation. As examples, the learner L may be a student (a student at any institution from elementary school to college, or a vocational school), someone studying for a qualification, a foreign language learner, or a student on an e-learning program. Accordingly, the subject of the questions may also be appropriately selected according to the implementation. The correct answer data is composed of information for judging whether an answer to a question is correct or incorrect.

However, as long as it is possible to acquire questions according to difficulty level, the configuration of the question database 125 is not limited to the example described above and may be appropriately determined according to the implementation. If it is possible, as with a calculation problem or a language question for example, to specify the correct answer from a specified question itself, information on the correct answer may be omitted. When a plurality of types of questions are included, each record may further include fields that identify the question format, subject, and the like. Alternatively, different types of question database 125 may be separately prepared, for different question formats, subjects, or the like.

Each software module of the learning system 1 is described in detail in the "Example Operation" given below. Note that for the present embodiment, an example where each software module of the learning system 1 is implemented by a general-purpose CPU is described. However, some or all of the software modules described above may be implemented by one or a plurality of dedicated processors. Regarding the software configuration of the learning system 1, software modules may be omitted, replaced, and/or added as appropriate according to the implementation.

3. Example Operation

Figure 5:
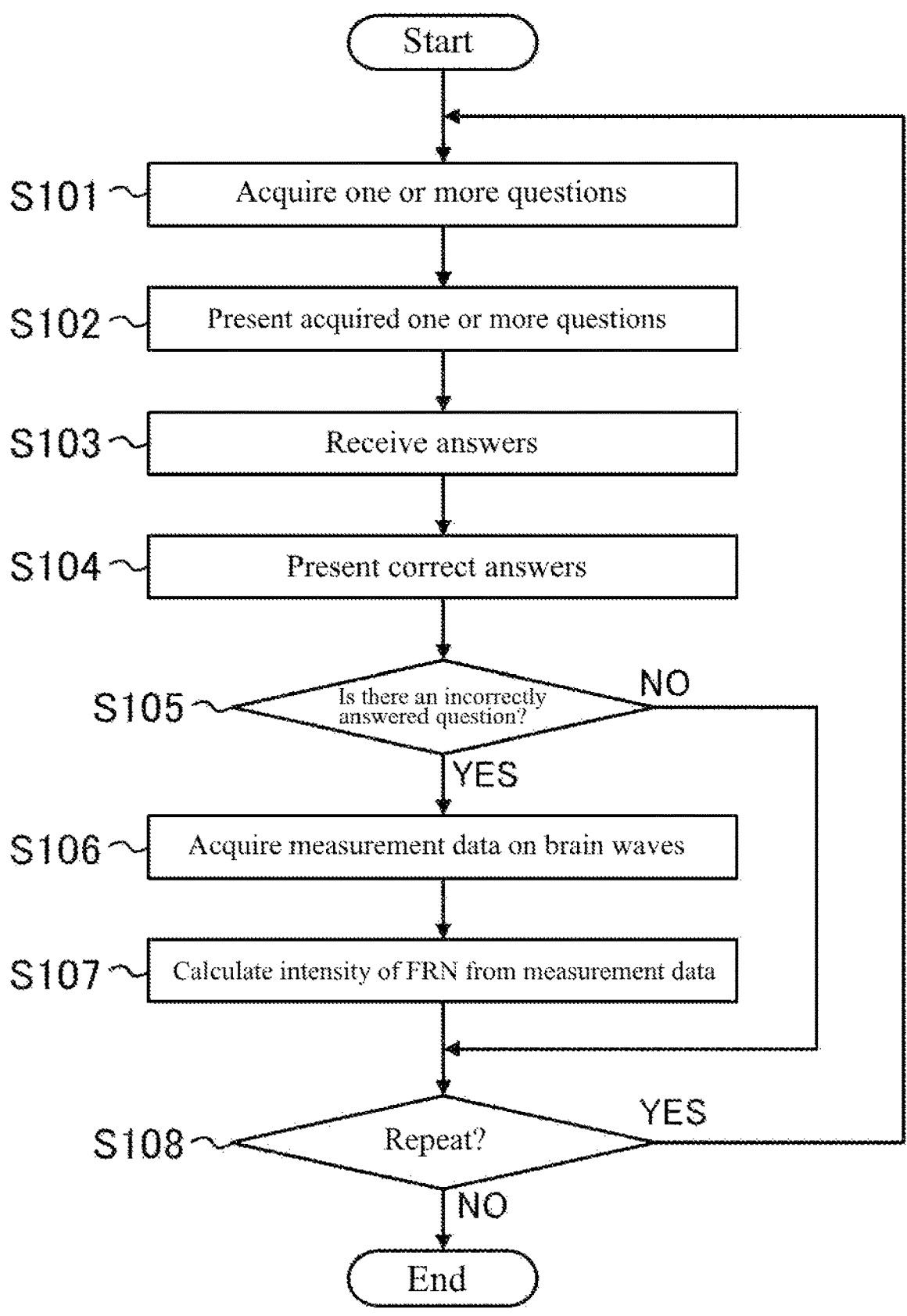
FIG. 5 is a flowchart depicting an example of a processing procedure of the learning system according to the present embodiment.

FIG. 5 is a flowchart depicting an example of the processing procedure of the learning system 1 according to the present embodiment. The processing procedure of the learning system 1 described below is one example of a learning method. However, the processing procedure of the learning system 1 described below is merely one example, and each step in the procedure may be changed whenever possible. Also, in the processing procedure described below, steps may be omitted, replaced, and/or added as appropriate according to the implementation.

(Step S101)

In step 101, the control unit 11 operates as the question acquisition unit 111 and acquires one or more questions. The method used to acquire the questions may be appropriately selected according to the implementation. In the present embodiment, the control unit 11 can acquire one or more questions by accessing the question database 125.

At an initial stage, the question(s) to be acquired may be freely decided. As one example, the control unit 11 may acquire one or more questions by randomly selecting one or more records from the question database 125. As another example, the control unit 11 may determine the difficulty level of the questions to be acquired by an any method, as examples, according to a designation by the learner L or a setting value in the learning program 81, and then acquire one or more questions by freely selecting records including questions of the determined difficulty level from the question database 125. If a record of previous use of the learning system 1 exists, the difficulty level of the questions to be acquired may be determined according to the difficulty level of the questions presented the previous time.

When a plurality of questions are acquired, the difficulty level of all of the acquired questions may be the same, or the difficulty level of some of the acquired questions may differ to other acquired questions. When questions of different difficulty levels are acquired, the control unit 11 may determine the range of difficulty levels according to an any method and acquire one or more questions by selecting records including questions of difficulty levels belonging to the determined range from the question database 125. Questions acquired at this initial stage are one example of "first questions" for the present invention. After acquiring one or more questions, the control unit 11 advances the processing to the next step, step S102.

(Step S102)

In step S102, the control unit 11 operates as the question presentation unit 112 and presents the learner L with the one or more questions that were acquired.

The method of presenting the questions may be appropriately selected according to the implementation. As one example, when the output device 15 includes a speaker, the control unit 11 may present the acquired one or more questions to the learner L by outputting the acquired one or more questions via the speaker as audio. As another example, when the output device 15 includes a display, the control unit 11 may present the acquired one or more questions to the learner L by displaying the acquired one or more questions on the display. The output destination of the questions is not necessarily the same device. As one example, when the learner L accesses the learning system 1 using a user terminal including an output device, the control unit 11 may present the acquired one or more questions to the learner L via the output device of the user terminal. After presenting the question(s), the control unit 11 advances the processing to the next step, step S103.

(Step S103)

In step S103, the control unit 11 operates as the answer reception unit 113 and receives answers from the learner L to the presented questions.

A method of receiving answers may be appropriately selected according to the implementation. As one example, if the input device 14 includes a microphone, the control unit 11 may receive answers as audio via the microphone. As another example, if the input device 14 includes an operation device such as a mouse, a keyboard, or a touch panel display, the control unit 11 may receive answers via operations of the operation device. The device that receives an answer is not necessarily the same device. As one example, when the learner L accesses the learning system 1 using a user terminal including an input device, the control unit 11 may indirectly receive answers to the presented questions via the input device of the user terminal. After receiving the answers, the control unit 11 advances the processing to the next step, step S104.

(Step S104)

In step S104, the control unit 11 operates as the correct answer presentation unit 114 and presents the learner L with the correct answers to the provided questions.

The presented content of the correct answer may be appropriately determined according to the implementation. As one example, the control unit 11 may present the information in the correct answer field of the record selected in step S101 as it is. As another example, the control unit 11 may determine whether the learner L's answer is correct or incorrect by checking the answer received from the learner L against the information on the correct answer. After this, the control unit 11 may present the determination result to the learner L as information on the correct answer. If the information on the correct answer includes an explanation, the control unit 11 may present the explanation together with the determination result to the learner L. In the same way as step S102, the method of presenting the correct answer may be appropriately selected according to the implementation. The output destination of the correct answer may be the same as the output destination of the question, or may differ. After the correct answer has been presented, the control unit 11 advances the processing to the next step, step S105.

(Step S105)

In step S105, the control unit 11 determines a branch destination of the processing depending on whether the learner L incorrectly answered a question in the series of learning processes in steps S102 to S104. When it was determined in step S104 whether the learner L's answers were correct or incorrect, the control unit 11 may use the result of that determination to determine the branch destination of the processing. As a different example, the control unit 11 may determine whether the learner L's answers were correct or incorrect separately to the processing in step S104 and determine the branch destination of the processing according to the result of this determination. If there is an incorrectly answered question, the control unit 11 advances the processing to the next step, step S106. On the other hand, if there are no incorrectly answered questions, the control unit 11 advances the processing to step S108.

(Step S106)

In step S106, the control unit 11 operates as the intensity calculation unit 115 and acquires measurement data generated by measuring the brain activity of the learner L when the correct answer was presented by the processing in step S104.

In the present embodiment, the control unit 11 can acquire the measurement data from the measurement sensor S. However, the route for acquiring the measurement data is not limited to the example given here. The measurement sensor S may be connected to another computer and the control unit 11 may acquire the measurement data from this other computer. The timing at which the measurement sensor S measures brain activity may be appropriately determined so as to include at least a 300 ms period starting from the instant the correct answer was presented by step S104. After acquiring the measurement data, the control unit 11 advances the processing to the next step, step S107.

(Step S107)

In step S107, the control unit 11 operates as the intensity calculation unit 115 and calculates the intensity of the feedback-related negativity from the measurement data acquired by the processing in step S106. As examples of a method of calculating the intensity of the feedback-related negativity, it is possible to adopt an arithmetic averaging method that averages a plurality of measurement data or a machine learning method that calculates the intensity from single trial data. After calculating the intensity of the feedback-related negativity, the control unit 11 advances the processing to the next step, step S108.

(Step S108)

At step S108, the control unit 11 determines whether to repeat the series of learning processes from steps S102 to S104.

The criteria for repeating the processes may be set freely. As one example, the learner L may select whether to repeat the series of learning processes. In this case, the control unit 11 may determine whether to repeat the series of learning processes according to the learner L's selection. As a different example, a number of iterations may be set. The number of iterations may be provided by any method, such as a designation by the learner L or a set value included in the learning program 81. In this case, the control unit 11 may determine whether to repeat the series of learning processes according to whether the executed number of iterations of the series of learning processes composed of steps S102 to S104 has reached a set number of iterations.

When a determination to not repeat the processing has been taken, the control unit 11 ends the processing procedure according to this example operation. Note that if a determination to not repeat the processing was taken at the step S104 stage based on the criteria described above, the control unit 11 may omit the processing in steps S105 to S107 and end the processing procedure according to this example operation. On the other hand, when a determination to repeat the processing has been taken, the control unit 11 causes the processing to return to step S101 and repeats the series of learning processes.

When the series of processes is repeated, if the processing in steps S106 and S107 was performed during the previous iteration, in step S101 of the current iteration, the control unit 11 may acquire one or more questions according to the intensity of the feedback-related negativity calculated in the previous iteration and the incorrectly answered question(s). That is, the control unit 11 may determine the question setting strategy based on the feedback-related negativity. The questions acquired in the previous iteration are examples of "first questions" for the present invention, and the questions acquired in the current iteration are examples of "second questions". When the series of processes is repeated for a further iteration, questions acquired in the current iteration may be treated as "first questions" with respect to this further iteration.

The question setting strategy based on the feedback-related negativity may be determined according to any rules. As indicated in the "Experimental Example" described later, the intensity of the feedback-related negativity is higher for questions where the learning motivation is high and is lower for questions where the learning motivation is low. Any rules may be provided based on this observation.

As one example, the controller 11 may compare the calculated intensity of the feedback-related negativity with a first threshold. When the calculated intensity of the feedback-related negativity exceeds the first threshold, the control unit 11 may acquire another question with the same difficulty level as the question for which an incorrect answer was given in the previous iteration from the question database 125 as the question in the current iteration. When the calculated intensity of the feedback-related negativity is equal to the first threshold, the control unit 11 may acquire another question of the same difficulty level as the question for which an incorrect answer was given in the previous iteration as the question of the current iteration. By using this strategy, it is possible to continue setting questions with a difficulty level that has been evaluated, based on the intensity of the feedback-related negativity, as providing high learning motivation for the learner L.

As a different example, the control unit 11 may compare the calculated intensity of the feedback-related negativity with a second threshold. If the calculated intensity of the feedback-related negativity is less than the second threshold, the control unit 11 may acquire another question, with a different difficulty level to the question answered incorrectly in the previous iteration, from the question database 125 as the question of the current iteration. When the calculated intensity of the feedback-related negativity is equal to the second threshold, the control unit 11 may acquire another question with a different difficulty level to the question answered incorrectly in the previous iteration as the question of the current iteration. By setting, as the next question to be presented, a question with a different difficulty level to a question evaluated based on the intensity of the feedback-related negativity as providing low learning motivation to the learner L, it is possible to find a question with a difficulty level for which the learning motivation is high.

Note that whether to increase or decrease the difficulty level from the question in the previous iteration may be freely determined. As one example, the control unit 11 may decide whether to increase or decrease the difficulty level from the level of the question(s) in the previous iteration according to the performance (that is, the percentage of correct answers) of the learner L up to the current iteration. In more detail, if the percentage of correct answers for the difficulty level of the question answered incorrectly in the previous iteration exceeds a threshold, the control unit 11 may acquire a question with a higher degree of difficulty than the question answered incorrectly in the previous iteration. On the other hand, if the percentage of correct answers for the difficulty level of a question that was answered incorrectly in the previous iteration is below the threshold, the control unit 11 may acquire a question with a lower difficulty level than the question that was answered incorrectly in the previous iteration. If the percentage of correct answers is equal to the threshold, either of these strategies may be selected as appropriate. As a different example, when acquiring a plurality of questions, the control unit 11 may acquire one or more questions with a higher difficulty level and one or more questions with a lower difficulty level than the questions in the previous iteration.

On the other hand, if the processing in steps S106 and S107 were not executed in the previous iteration, in step S101 of the current iteration, the control unit 11 may acquire one or more questions according to any method. As one example, the control unit 11 may acquire one or more questions using a similar method to step S101 in the previous iteration.

After acquiring one or more questions, the control unit 11 may execute the processing of steps S102 to S107 for the acquired questions in the same way as the previous iteration. That is, in step S102, the control unit 11 presents the one or more questions that have been acquired in the current iteration to the learner L. In step S103, the control unit 11 receives answer(s) to the presented question(s) from the learner L. After reception of the answer(s) is complete, in step S104, the control unit 11 presents correct answer(s) for the presented question(s) to the learner L. If the learner L's answer(s) to the presented question(s) is/are incorrect, the control unit 11 acquires measurement data generated by measuring the brain activity of the learner L when the correct answer(s) were presented (step S106) and calculates the intensity of the feedback-related negativity from the acquired measurement data (step S107).

The above series of processes may be repeated for two or more iterations by the processing in step S108. In this case, in step S108, the control unit 11 may operate as the stopping unit 116 and determine whether the intensity of the feedback-related negativity calculated in each iteration has continuously been below than a third threshold. A case where the intensity of the feedback-related negativity is equal to the third threshold may be treated in the same way as cases where the potential is below the third threshold or cases where the potential is above the third threshold. The criteria for recognizing whether the state qualifies as "continuously" may be determined freely. As one example, when the number of times the calculated intensity of the feedback-related negativity is continuously lower than the third threshold exceeds a set number of times, the control unit 11 may determine that the calculated intensity of the feedback-related negativity is continuously lower than the third threshold. When the calculated intensity of the feedback-related negativity is continuously lower than the third threshold, the control unit 11 may determine to not repeat the series of processes (that is, to stop the repeated presentation of questions), and end the processing procedure according to this example operation. By doing so, it is possible, when the learning motivation of the learner L is continuously evaluated as being low based on the intensity of the feedback-related negativity, to stop presenting questions and encourage the learner L to take a break.

Note that the first threshold, the second threshold, and the third threshold mentioned above may be the same value or different values. When rules are to be adopted simultaneously, the respective thresholds may be determined so that the rules are not inconsistent. As one example, the first threshold may be equal to or greater than the second threshold, and the third threshold may be equal to or less than the first threshold and the second threshold. Each threshold may be provided freely, as examples, according to a designation by the learner L and/or set values inside the learning program 81. If the calculated intensity of the feedback-related negativity does not correspond to any of the cases described above (for example, when the first threshold is greater than the second threshold and the intensity of the FRN is between the first and second thresholds), in step S101, the control unit 11 may select questions according to an any method in the same way as in the initial stage.

Features

As described above, the learning system 1 according to the present embodiment is capable, when repeating a series of processes composed of step S101 to step S107 described above, of deciding the next questions to be presented based on the intensity of the feedback-related negativity induced when the learner L was presented with the correct answer of a question that was incorrectly answered. Using the intensity of the feedback-related negativity, it is possible to objectively evaluate the learning motivation of the learner L. Since the intensity of the feedback-related negativity can be stably measured for different subjects and can be measured even with a small number of electrodes, measurement and calculation can be performed comparatively easily. This means that according to the present embodiment, it is possible to adopt a question setting strategy that increases the learning motivation of the learner L easily and appropriately using brain waves.

4. Modifications

Although embodiments of the present invention have been described above in detail, the description given thus far is in every way a mere example of the present invention. It should be obvious that various improvements or modifications can be made without departing from the scope of the present invention. As examples, the following changes can be made. Note that in the following description, the same reference numerals are used for the same components as those in the embodiment described above, and description of points that are the same as in the above embodiment is omitted as appropriate. The following modifications can also be combined as appropriate.
<4.1>
In the embodiment described above, the question database 125 is present inside the learning system 1. However, the placed location of the question database 125 is not limited to the example described above. As a different example, the question database 125 may be present in another computer, such as NAS (Network Attached Storage). In this case, in step S101 described above, the control unit 11 may acquire questions by accessing the other computer as appropriate.

In the embodiment described above, the learning system 1 acquires the questions from the question database 125. However, the method of acquiring the questions is not limited to this example. As a different example, in step S101, the control unit 11 may generate a question by any method. As one example of a generation method, when a calculation problem is to be set, the control unit 11 may generate a question by appropriately inputting numerical values into a template. In this case, the control unit 11 may present the generated question to the learner L in step S102. In the same way, in step S104, the control unit 11 may appropriately solve the presented question to generate correct answer information for the presented question and present this generated correct answer information.

Also, in the embodiment described above, a trained model generated by machine learning may be used to determine a question setting strategy based on feedback-related negativity. That is, a configuration may be used where a question setting strategy that is decided based on the intensity of the feedback-related negativity is determined using a machine learning technique. As one example, in step S101 described above, the control unit 11 may use a trained model to acquire one or more questions in accordance with the calculated intensity of feedback-related negativity and questions that were incorrectly answered. The trained model may be appropriately generated to estimate the difficulty level of questions that will increase the learning motivation of the learner from the calculated intensity of the feedback-related negativity and the difficulty level of the incorrectly answered questions.
<4.2>
Also, in the embodiment described above, the learning system 1 may be configured to calculate the intensity of the feedback-related negativity when the correct answer was presented regardless of whether the answer was incorrect. In this case, the processing in step S105 may be omitted from the above processing procedure.

In addition, in the embodiment described above, the learning system 1 may generate history information on the calculated intensity of the feedback-related negativity. Using this history information, it is possible to verify after the fact whether the learner L tackled provided questions with high learning motivation.
<4.3>
In the embodiments described above, the processing that stops the repeating of the processes in response to the calculated intensity of the feedback-related negativity being continuously lower than the third threshold may be omitted. In this case, the stopping unit 116 may be omitted from the software configuration of the learning system 1.

Also, in the embodiment described above, the question setting strategy is determined based on the intensity of the feedback-related negativity obtained in one iteration of the processes. However, the way in which the intensity of the feedback-related negativity is used to determine the question setting strategy is not limited to this example. The learning system 1 may be configured to determine the question setting strategy based on the intensity of the feedback-related negativity obtained in multiple iterations of the processes.

5. Experimental Example

To verify whether the intensity of the feedback-related negativity induced when the correct answer to an incorrectly answered question is presented to the learner is valid as an objective index for evaluating learning motivation, a brain wave measuring experiment was conducted under the following conditions.
<Experiment Conditions>
Subjects: 11 people (aged 20 to 40)
Submitted questions: Calculation problems (five difficulty levels, where the simplest problem is the addition of single-digit numbers, and the most difficult problem is the addition of three-digit numbers)
Measurement sensor: Polymate Mini AP108
Method of presenting correct answers: Audio (auditory feedback indicating whether the answer was correct)

To change the learning motivation, calculation problems were presented to the subjects in a game format where a point is added for each correct answer, targets (that is, a target setting time and target points) are set, and bonus points are added for the number of consecutive correct answers and any remaining time, with a ranking being displayed based on the acquired points. The amplitude of the feedback-related negativity induced when the correct answer for an incorrectly answered question was presented to the learner was then measured. After answering calculation problems of every difficulty level, the subjects were asked to rank the calculation problems of each difficulty level (A) in order of questions for which the learner felt high learning motivation to get a high score, and (B) in order of questions that the learner felt were suited to his/her level.

Figure 6A:
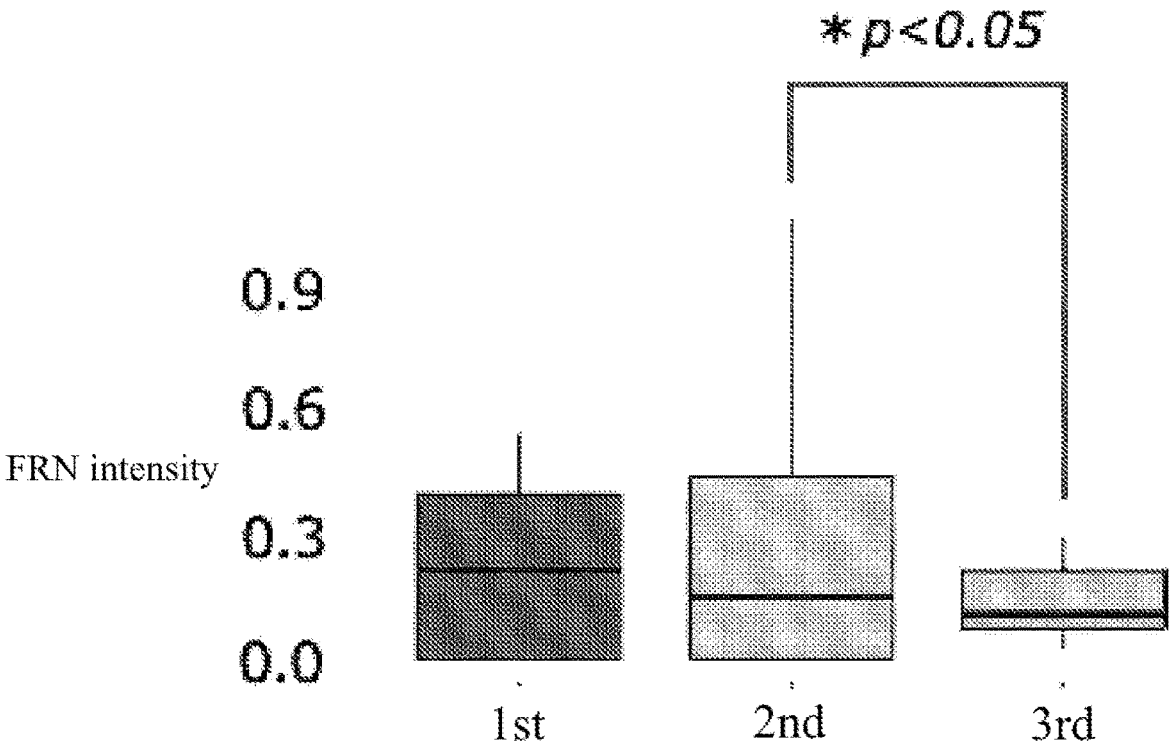
FIG. 6A depicts a result of comparing intensity of FRN induced when correct answers to incorrectly answered questions were fed back to subjects, in order of ranking of learning motivation by subjects (that is, whether the subjects were highly motivated to get a high score)
Figure 6B:
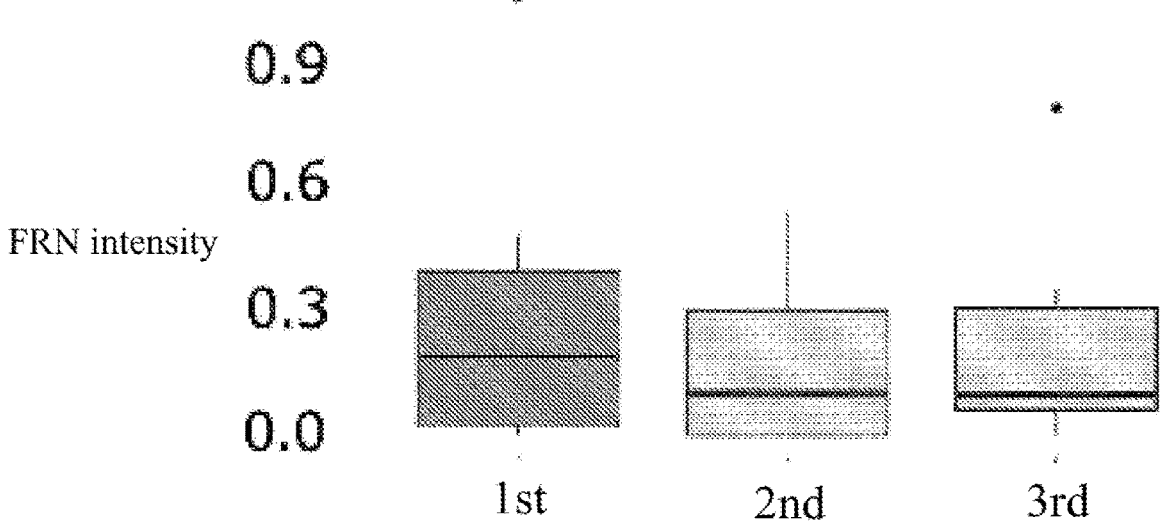
FIG. 6B depicts a result of comparing intensity of FRN induced when correct answers to incorrectly answered questions were fed back to subjects, in order of ranking based on self-evaluation the subjects (that is, whether questions were suited to the subject's own level).

FIG. 6A depicts the result of comparing the amplitudes of feedback-related negativity induced when correct answers to incorrectly answered questions were fed back to subjects, in order of a ranking of the subjects' learning motivation (that is, whether the subjects were highly motivated to get a high score). FIG. 6B depicts the result of comparing the amplitudes of feedback-related negativity induced when the correct answers to incorrectly answered questions were fed back to subjects, in order of a ranking based on self-evaluation by the subjects (that is, whether the questions were suited to the learner's own level).

As depicted in FIG. 6A, a significant difference in the amplitude of the feedback-related negativity was observed between questions with a difficulty level evaluated as providing high learning motivation (ranked first and second), and questions with a difficulty level evaluated as providing low learning motivation (ranked third or lower). On the other hand, such significant difference was not observed for questions ranked according to self-assessment. From these experimental results, it was understood that the intensity of the feedback-related negativity is useful as an objective index for evaluating learning motivation. It was also understood that the learner's self-evaluation does not always match learning motivation. Accordingly, it was understood that to adopt a question setting strategy that increases the learning motivation of learners, it is beneficial to determine the difficulty level based on the intensity of the feedback-related negativity, rather than determining the difficulty level based on self-evaluation.

LIST OF REFERENCE NUMERALS

1 Learning system
11 Control unit
12 Storage unit
13 External interface
14 Input device
15 Output device
16 Drive
81 Learning program
91 Storage medium
111 Question acquisition unit
112 Question presentation unit
113 Answer reception unit
114 Correct answer presentation unit
115 Intensity calculation unit
116 Stopping unit
125 Question database
S Measurement sensor
L Learner

What is claimed is:

1. A learning system comprising:
a sensor; and
at least one processor and a memory, configured to cooperate to perform operations comprising:
acquiring one or more first questions;
presenting the acquired one or more first questions to a learner via at least one of a display and a speaker;
receiving answers to the presented first questions from the learner via a user interface;
presenting correct answers for the first questions to the learner after the answers to the first questions have been received via at least one of the display and the speaker;
acquiring, in a case where an answer by the learner to a first question is incorrect, measurement data generated by measuring, via the sensor, brain waves indicative of brain activity of the learner in a case where the correct answer was presented; and
calculating an intensity of feedback-related negativity from the acquired measurement data;
acquiring one or more second questions in accordance with the calculated intensity of feedback-related negativity and the first question that was incorrectly answered;
presenting the acquired one or more second questions to the learner via at least one of the display and the speaker; and
receiving an answer to each presented second question from the learner via the user interface.

2. The learning system according to claim 1, wherein the operations further comprise, in a case where the calculated intensity of the feedback-related negativity exceeds a first threshold, acquiring as the second questions, other questions of the same level as the first question that was incorrectly answered.

3. The learning system according to claim 1, wherein the operations further comprise, in a case where the calculated intensity of the feedback-related negativity is below a second threshold, acquiring as the second questions, other questions of a different level to the first question that was incorrectly answered.

4. The learning system according to claim 1, wherein the operations further comprise, in a case where presentation of questions to the learner is repeated and the calculated intensity of the feedback-related negativity is continuously lower than a third threshold, stopping the repeated presentation of questions.

5. A learning method performed by a computer comprising a processor and memory, the computer being operably connected to a sensor, the method comprising:
acquiring one or more first questions;
presenting the acquired one or more first questions to a learner via at least one of a display and a speaker operably connected to the computer;
receiving answers to the presented first questions from the learner via a user interface provided by the computer;
presenting correct answers for the first questions to the learner after the answers to the first questions have been received via at least one of the display and the speaker;
acquiring, in a case where an answer by the learner to a first question is incorrect, measurement data generated by measuring, via the sensor, brain waves indicative of brain activity of the learner in a case where the correct answer was presented;
calculating an intensity of feedback-related negativity from the acquired measurement data;

acquiring one or more second questions in accordance with the calculated intensity of feedback-related negativity and the first question that was incorrectly answered;

presenting the acquired one or more second questions to the learner via at least one of the display and the speaker; and receiving an answer to each presented second question from the learner via the user interface.

6. The learning method according to claim 5, further comprising in a case where the calculated intensity of the feedback-related negativity exceeds a first threshold, acquiring as the second questions, other questions of the same level as the first question that was incorrectly answered.

7. The learning method according to claim 5, further comprising in a case where the calculated intensity of the feedback-related negativity is below a second threshold, acquiring as the second questions, other questions of a different level to the first question that was incorrectly answered.

8. The learning method according to claim 5, further comprising in a case where presentation of questions to the learner is repeated and the calculated intensity of the feedback-related negativity is continuously lower than a third threshold, stopping the repeated presentation of questions.

9. A non-transitory computer readable storage medium tangibly storing a learning program that, when executed by a processor, causes the processor to perform operations comprising:

acquiring one or more first questions;

presenting the acquired one or more first questions to a learner via at least one of a display and a speaker;

receiving answers to the presented first questions from the learner via a user interface;

presenting correct answers for the first questions to the learner after the answers to the first questions have been received via at least one of the display and the speaker;

acquiring, in a case where an answer by the learner to a first question is incorrect, measurement data generated by measuring, via a sensor, brain waves indicative of brain activity of the learner in a case where the correct answer was presented;

calculating an intensity of feedback-related negativity from the acquired measurement data;

acquiring one or more second questions in accordance with the calculated intensity of feedback-related negativity and the first question that was incorrectly answered;

presenting the acquired one or more second questions to the learner via at least one of the display and the speaker; and receiving an answer to each presented second question from the learner via the user interface.

10. The non-transitory computer readable storage medium according to claim 9, wherein in a case where the calculated intensity of the feedback-related negativity exceeds a first threshold, other questions of the same level as the first question that was incorrectly answered are acquired as the second questions.

11. The non-transitory computer readable storage medium according to claim 9, wherein in a case where the calculated intensity of the feedback-related negativity is below a second threshold, other questions of a different level to the first question that was incorrectly answered are acquired as the second questions.

12. The non-transitory computer readable storage medium according to claim 9, wherein in a case where presentation of questions to the learner is repeated and the calculated intensity of the feedback-related negativity is continuously lower than a third threshold, the repeated presentation of questions is stopped.

* * * * *